(12) United States Patent
Smith

(10) Patent No.: US 8,293,291 B2
(45) Date of Patent: Oct. 23, 2012

(54) METHODS AND COMPOSITIONS FOR REDUCING THE APPEARANCE OF DYNAMIC FACIAL WRINKLES

(76) Inventor: Walter P. Smith, New Canaan, CT (US)

( * ) Notice: Subject to any disclaimer, the term of this patent is extended or adjusted under 35 U.S.C. 154(b) by 1022 days.

(21) Appl. No.: 12/213,860

(22) Filed: Jun. 25, 2008

(65) Prior Publication Data

US 2009/0104174 A1 Apr. 23, 2009

Related U.S. Application Data

(60) Provisional application No. 60/929,371, filed on Jun. 25, 2007.

(51) Int. Cl.
*A61K 36/00* (2006.01)
*A61K 36/06* (2006.01)
(52) U.S. Cl. .......... 424/769; 424/725; 424/195.16
(58) Field of Classification Search .......... None
See application file for complete search history.

(56) References Cited

U.S. PATENT DOCUMENTS

| | | | | |
|---|---|---|---|---|
| 5,676,948 A | * | 10/1997 | Bonte et al. | 424/769 |
| 7,252,831 B2 | * | 8/2007 | Khaiat et al. | 424/401 |
| 7,666,442 B2 | * | 2/2010 | Morariu | 424/401 |
| 7,695,741 B2 | * | 4/2010 | Lee et al. | 424/725 |
| 2004/0126352 A1 | * | 7/2004 | Jones | 424/74 |
| 2006/0198800 A1 | * | 9/2006 | Dilallo et al. | 424/59 |
| 2007/0148186 A1 | * | 6/2007 | Ketzis | 424/195.11 |
| 2008/0070993 A1 | * | 3/2008 | Borbely | 514/777 |
| 2008/0089958 A1 | * | 4/2008 | Diehl et al. | 424/725 |

* cited by examiner

*Primary Examiner* — Christopher R. Tate
(74) *Attorney, Agent, or Firm* — Louis C. Paul

(57) ABSTRACT

The present invention relates to methods and compositions for reducing the appearance of dynamic facial wrinkles by administering oral and/or topical compositions comprising therapeutically-effective amounts of extracts of one or more relaxing herbal agents ("RHAs") alone or in combination with one or more extracts of an edible solanaceous glycoalkaloid-containing plant ("ESGP") or an edible glycoalkaloid-containing fungus ("EGF") selected from plant species in the genus *Solanum* and mushrooms. RHAs are selected from the group consisting of extracts of *Q. amara, E. angustifolia, P. oleracea, M. dubia, P. orientalis* and *A. muscaria* and plant species from the genus *Valeriana, Passiflora, Verbascum, Scutellaria, Cypripedium, Magnolia, Atriplex* and *Symphytum*. Additionally, the methods of the present invention may comprise exfoliating the skin, preferably with at least one acid protease enzyme.

10 Claims, No Drawings

METHODS AND COMPOSITIONS FOR REDUCING THE APPEARANCE OF DYNAMIC FACIAL WRINKLES

CROSS REFERENCE TO RELATED APPLICATIONS

This application claims priority under 35 U.S.C. §119 to U.S. Provisional Application Ser. No. 60/929,371, filed on Jun. 25, 2007, the disclosure of which is hereby expressly incorporated by reference in its entirety.

FIELD OF INVENTION

The present invention relates to methods and compositions for reducing the appearance of facial lines and wrinkles, particularly deep dynamic facial wrinkles.

STATEMENT OF FEDERALLY-SPONSORED RESEARCH

Not applicable.

BACKGROUND OF THE INVENTION

Skin aging and wrinkling is a multifactor process. The formation of lines and wrinkles can be attributed to both extrinsic and intrinsic causes. Extrinsic causes include exposure to ultraviolet radiation and unquenched reactive oxygen species, smoke and other pollutants. Intrinsic factors include degradation of the skin matrix, loss of volume (fat and bone) and muscle tone.

With each smile, squint, laugh, or frown, the contraction of facial muscles causes dynamic wrinkles to appear on the face. In chronologically-younger skin, these lines dissipate quickly and are not prominent. However, with age, the lines become deeper and appear more noticeable. Most commonly, they are manifested as deep furrows between the eyebrows ("frown lines"), at the sides of the eyes ("crow's feet"), and across the forehead ("glabellar lines").

The biochemistry and biomechanics of skeletal muscle contraction are well-characterized. Contraction is initiated by an electric signal (action potential) transmitted by the motor neuron. At the neuromuscular junction, the action potential causes vesicles to release the neurotransmitter acetylcholine ("Ach") which, in turn, diffuses across the synapse between the nerve ending and the sarcolemma, the membrane of muscle fibers. ACh binds to ACh receptors, triggering the action potential to spread, and causing a release of calcium ions.

Botulinum Toxin Type A (BTX-A), is a $Zn^{2+}$-dependent endoprotease neurotoxic protein obtained from the bacterium *Clostridium botulinum*. BTX-A produces muscle relaxation by binding to and entering the motor neuron where it cleaves SNAP-25, a SNARE protein. (Together with synaptobrevin and syntaxin, SNAP-25 is integral to the $Ca^{2+}$-regulated exocytosis (release) of acetylcholine by the motor neuron.)

BTX-A was first approved by the US Food and Drug Administration for the treatment of strabismus, blepharospasm and hemifacial spasm in patients over 12 years old. In 2002, FDA approved BTX-A as a treatment for glabellar lines associated with corrugator and/or procerus muscle activity in patients 18 to 65 years of age. Inhibition of muscle contraction by BTX-A is reported to last typically for about four to six months.

It is known to those of ordinary skill in the art that muscle groups differ in their sensitivity to muscle relaxants. Muscles in the periorbital and glabellar areas are particularly sensitive to ACh and thus susceptible to effective treatment by agents that block Ach release. See, e.g., the review article published by L. Vimal and O. Oladapo, "Pharmacology of Non-Depolarising Muscle Relaxants" in Issue 5, Article 7 of *Update in Anaesthesia*, the electronic educational journal of World Anaesthesia and the World Federation of Societies of Anaesthesiologists. http://www.nda.ox.ac.uk/wfsa/html/u05/u05_012.htm accessed Jun. 20, 2007.

That certain edible solanaceous glycoalkaloid-containing plants (ESGPs)—in particular potatoes, eggplants, and tomatoes—increase the duration of action of anesthetics and muscle relaxants has been reported in the scientific literature. Researchers at the University of Chicago reported that potatoes, eggplants, and tomatoes inhibit the activity of enzymes that breakdown ACh and a structurally-related neurotransmitter butyrylcholine which acts on several Ach receptors. See, DS McGehee et al. "Cholinesterase Inhibition by Potato Glycoalkaloids Slows Mivacurium Metaboli" Anesthesiology, Vol. 93, No. 2, pp. 510-519 (August 2000).

Red and green peppers are edible solanaceous plants containing glycoalkaloids. P G Jones and G R Fenwick, "The glycoalkaloid content of some edible solanaceous fruits and potato products," *Journal of the Science of Food and Agriculture*, Vol. 32, No. 4, pp. 419-421 (1981).

*Ziziphus ziziphus* (also known as *Z. jujuba*, Jujube, Red Date and Chinese Date) has long been cultivated in China. In the US, it is grown in the West (California and Utah), the Southeast (Alabama, Florida and Georgia) and the Gulf Coast (Texas and Louisiana). In traditional Chinese and Korean medicine, the Jujube fruit was ground into powder and ingested, reducing stress.

The mature Jujube fruit, which is dark red to purplish-black and wrinkled and thus similar in appearance to the date, is rich in alkaloids. See, R. Ziyaev et al., "Alkaloids of *Ziziphus jujuba*: the structure of juziphine and juzirine," *Chemistry of Natural Compounds*, Vol. 13, No. 2, pp. 204-207 (1977); see also, M. Tripathi, "Cyclopeptide alkaloids from *Zizyphus jujuba*," *Fitoterapia*, Vol. 72, No. 5, pp. 507-510 (2001). *Z. jujube* is listed on the ingredient labeling Age Defying Continual Eye Treat sold by Ahava.

U.S. Pat. No. 6,866,856 (assigned to Avon) teaches topical compositions comprising toosendanin and azadirachtin. (To the extent pertinent, the disclosures of all granted US patents and published US patent applications cited are incorporated in their entirety by reference.) Mechanistically, these two limonoid constituents are described in the '856 Patent as inhibiting acetylcholine release, thereby relaxing the muscles involved facial movement and expression. Topical application of formulations comprising one or both of these limonoid constituents are taught to ameliorate, reduce, and/or eliminate wrinkles and/or fine lines.

Laboratoires Sérobiologiques markets Myoxinol, a biotransformed oligopeptide derived from the seeds of *Hibiscus esculentus* L. (okra), as a "natural alternative" to Botox injections. According to marketing materials, the compound works by inhibiting facial muscle contraction, preventing the formation of horizontal and vertical frown lines, crow's feet and naso-labial lines.

US Patent Application Publication No. 2006/0275351 (assigned to Estée Lauder) describes a topical delivery system comprising a dermal patch that generates electrical current when in contact with the skin and a skin beneficial peptide (e.g., Myoxinol) in a conductive fluid.

US Patent Application Publication No. 2007/0065396 teaches topical compositions comprising macqui berry (as well as extracts and salts thereof) in combination with dermorelaxants, compounds which are defined as relaxing the muscles directly beneath the skin. Among the disclosed dermorelaxants are Myoxinol, the limonoid constituents taught in U.S. Pat. No. 6,866,856 and boswellia extract.

Argireline (INCI Name: acetyl hexapeptide-3) is marketed by Lipotec, SA and distributed in North America by Centerchem. A Jun. 18, 2004 article in the *New York Times* entitled "New Creams Smooth Wrinkles, But They're Not Botox" quoted the CEO of Centerchem who described Argireline as having a "de-stressing effect on the skin". Among the many cosmetic products that contain Argireline are Revlon's Age Defying Makeups with Botafirm (a complex comprising the acetyl hexapeptide and botanical extracts)

U.S. Pat. No. 6,169,074 teaches three peptide sequences that mimic the activity of neurotoxins produced by *Clostridium botulinum* and *tetani*. Structurally, the peptides are comprised of amino acid fragments from the substrate binding domains selected from three proteins which bind to form a receptor for docking of synaptic vesicles to the plasma membranes of neuronal cells (i.e., SNAP-25, VAMP-2 and syntaxin).

US Patent Application Publication No. 2007/0048245 teaches a topical composition comprising an extract of *Acemella oleracea* and a dermal stimulating peptide (particularly, short-chained palmitoylated, tri-, tetra- and penta-, and oligopeptides). The *Acemella oleracea* extract, described as rapid acting muscle relaxant, is claimed to limit contraction of facial muscles and thereby increase the efficiency of peptides in reducing wrinkles associated with photodamage and aging.

A number of skincare products claim to reduce wrinkles in a manner similar to BTX-A. Examples include Klein-Becker's Strivectin-SD®; Avon's Anew Clinical Deep Crease Concentrate with Bo-Hylurox. Some of these products have been described in the popular media as "faux-tox" creams. See, e.g., A. Cassabianca, "Freeze—The New Faux-Tox Creams" (describing Freeze 24/7, Dr. Brandt's Crease Release, Bliss's No-Motion Lotion and DDF's Wrinkle Relax serum as containing "topical muscle relaxants") accessed on Jun. 20, 2007 www.filly.ca/health/beauty/skin_care/Freeze_Faux-Tox.asp.

Dr. Brandt's Crease Release and Dermadoctor's Immobile Lines products both contain gamma aminobutyric acid (GABA), a neurotransmitter that mediates muscle activation at the neuromuscular junction. According to the product description on the Dermadoctor website, Immobile Lines induces temporary topical muscle relaxation associated with facial expression, thereby visibly reducing expression lines near the eyes and on the forehead. See, http://www.dermadoctorskincare.com/immobilelines.html (accessed Jun. 20, 2007). Grant-X (formerly GranTox), an ingredient complex sold by Grant Industries, contains aminobutyric acid in combination with other botanical extracts (*Panax ginseng, Portulaca oleracea* and *Centella asiatica*). It is marketed as improving the appearance of facial fine lines and wrinkles.

Two product lines sold by L'Oréal and its Lancôme subsidiary, L'Oréal's Dermo-Expertise and Lancôme's Résolution D-Contraxol, claim a different muscle relaxant ingredient, magnesium gluconate. The February 2003 edition of *Vogue*, quotes Alan Meyers, Vice-President of R&D at L'Oréal USA: "Manganese [gluconate] has a relaxing effect on cells. When your face is flexing, it prevents the fibroblasts . . . from staying contracted."

The prior art is replete with topical "anti-aging" compositions containing a plethora of active ingredients, many purporting to be naturally-derived from botanical sources (e.g., antioxidants, hydroxy acids, retinoids and short chain peptide derivatives) and claiming to help reduce the appearance of signs of extrinsic and intrinsic aging.

The uses of hydroxy acids for purposes of exfoliation, increasing skin cell turnover and helping to reduce the appearance of wrinkles are well known to those of skill in the art and are described, for example, in a series of related patents to Van Scott and Yu. See, U.S. Pat. Nos. 5,654,336; 5,547,988; and 5,385,938 (glycolic acid); U.S. Pat. Nos. 5,690,967; 5,684,044; 5,674,899; 5,547,988; and 5,422,370 (lactic acid); U.S. Pat. No. 5,889,054 (salicylic acid); U.S. Pat. Nos. 5,674,903; 5,547,988; and 5,470,880 (citric acid); U.S. Pat. Nos. 5,643,961 and 5,591,774 (malic acid).

A series of related patents assigned to Active Organics, LP—U.S. Pat. Nos. 5,976,556; 6,569,437; and 6,656,701—describe the uses of one or more acid protease enzymes in combination with an acidic buffering system that enhances epidermal exfoliation and/or epidermal cell renewal, thereby improving the texture or appearance of the skin.

In addition to topical products, and professional skin care treatments—including "light" cosmetic procedures performed by doctors, nurses, aestheticians and other trained technicians (e.g., micro-dermabrasion, chemical peels) and plastic surgery—consumers are increasingly seeking to treat the signs of aging through the use of ingested supplements, both in the form of capsules/tablets and beverages.

One example of an oral supplement taken by patients to decrease the appearance of aging is U.S. Pat. No. 5,804,594. The '594 patent teaches a method for the treatment and prevention of fine lines and wrinkles by oral administration of a pharmaceutical composition comprised of (i) a sugar compound that is converted to a glycosaminoglycan sufficient to thicken skin (e.g., N-acetylglucosamine), (ii) a primary antioxidant component in an amount sufficient to inhibit collagenase and elastase, (iii) at least one amino acid in an amount sufficient to assist in thickening skin (e.g., lysine or proline), (iv) a transition metal component in an amount effective to bind collagen and elastic fibers and thicken skin (e.g., zinc, manganese, copper), and (v) a catechin-based component in an amount sufficient to inhibit anti-collagen enzyme in the skin (e.g., a proanthocyanidin).

Commercially-available skin care nutritional supplements include: Murad Firm and Tone Dietary Supplement Pack (covered by the '594 patent); N. V. Perricone, M.D. Cosmeceuticals Skin & Total Body Dietary Supplements; RMX Essential from DDF.

The concept of skincare beverages is also known in the prior art. Borba has a line of nutraceutical water marketed as "Drinkable Skincare". L'Oréal and Coca-Cola are reported to be collaborating on a tea-based beverage that provides skin benefits to be marketed under the brand name Lumaé. U.S. Pat. No. 6,375,992 (assigned to Procter & Gamble) further illustrates a beverage that provides skin benefits. The '992 Patent teaches a method of hydrating the skin and thereby decreasing the appearance of fine lines and wrinkles by administering a substantially decaffeinated oral composition comprising substantially decaffeinated green teas, one or more flavanols and at least two of aloe, glycerol, and red grape extract.

U.S. Pat. No. 5,869,540 (to W P Smith) teaches a method of reducing the appearance of deep lines by oral administration (in the form of a tea) of an herbal relaxant agent, an aqueous extract of valerian root. The '540 Patent further teaches a method for reducing the visible signs of aging induced by stress-related tension by topical administration of a composition comprising an aqueous extract of valerian (genus *Valeriana*), passion flower (genus *Passiflora*), mullein (genus *Verbascum*), skullcap (genus *Scutellaria*), lady's slipper (genus

*Cypripedium*), magnolia (genus *Magnolia*), arrach (genus *Atriplex*) or comfrey (genus *Symphytum*). (Collectively, the above listed herbs are referred to, together with other herbs, as relaxant herbal agents ("RHAs")). In addition, the '540 Patent teaches a combined method of treating stress-induced deep lines by a combination regimen of drinking valerian-infused tea and topically applying a composition comprising one of the above-listed RHAs.

The present invention is an improvement on the methods described in U.S. Pat. No. 5,869,540. RHAs not heretofore disclosed are claimed. Additionally, surprisingly and unexpectedly, it has been found that the administration of the RHAs disclosed in the '540 Patent in combination with ESGPs or edible glycoalkaloid-containing fungi ("EGFs") and/or in combination with an exfoliating step, are more effective methods for reducing in the appearance of dynamic facial wrinkles.

For over two millennia, *Valeriana officinalis* has been used as a sedative and for the treatment of anxiety and insomnia. The predominant method of administering valerian has been and continues to be as a tea. Typically, from about 1.5 to about 3 grams of valerian root are steeped for five to ten minutes in 150 milliliters boiling water. Capsules have also been used, with a typical dose of from 300 to 1,800 milligrams by mouth. Medline Plus also reports use of valerian to treat stress, skin disorders, rheumatic pain, muscle pain, spasm and tension. See, www.nlm.nih.gov/medlineplus/druginfo/natural/patient-valerian.html accessed Jun. 20, 2007. See also, A. Herrera-Arellano, et al. "Polysomnographic evaluation of the hypnotic effect of Valeriana edulis standardized extract in patients suffering from insomnia" *Planta Med*. Vol. 67, pp. 695-699 (2001); P J Houghton, "The scientific basis for the reputed activity of Valerian" *J. Pharm. Pharmacol*. Vol. 51, pp. 505-512 (1999); P D Leathwood et al. "Aqueous extract of valerian root (*Valeriana officinalis* L.) improves sleep quality in man" *Pharmacol. Biochem. Behav.* Vol. 17, pp. 65-71 (1982).

U.S. Pat. No. 5,211,948 teaches a process for preparing powdered extracts of valerian root. The described process eliminates volatile odors produced by degradation products of valepotriates by adding an alcohol or acetone to the concentrated valerian extract. This step precipitates insoluble solids from the concentrated extract which are then separated from the extract. The extract is mixed with a carbohydrate and dried to obtain a powder.

U.S. Pat. No. 6,913,770 describes a process for isolating and purifying valerian extract by a hydroalcoholic extraction as well as the use of ingestible forms of valerian extract as a sedative, muscle relaxant and/or anxiolytic agent. U.S. Pat. Nos. 5,211,948 and 6,913,770 do not teach or suggest topical administration of valerian for reduction of dynamic facial lines.

The prior art teaches the use of mullein (*Verbascum*) as a muscle relaxant in treating asthma and other respiratory disorders involving irritation of the bronchi. See, http://www-.asthmaforthelayman.com/herbs.htm. accessed on Jun. 20, 2007.

U.S. Pat. No. 6,287,567 teaches an herbal beverage for relieving symptoms of fatigue, congestion, fever and asthma comprising equal portions of comfrey root, comfrey leaf, rosehip, goldenseal, bee pollen, spearmint, chickweed, chamomile flower, catnip, mullein, pennyroyal, eucalyptus, and licorice root.

U.S. Pat. No. 6,814,987 teaches methods for preventing, treating, and managing sleeplessness, restlessness and weight gain due to stress or lack of sleep, by administration of magnolia extracts soluble in a lower alcohol, water or hydroalcohol mixture.

*Quassia amara* (also known as Amargo, Bitter Ash and Bitter Wood) is a deciduous tree found in rainforests from southern Mexico to Brazil. Its bark and wood contain triterpenes, indole alkaloids, quassinoids, canthinones and scopoletin, ingredients which have been reported in the ethnobotany literature as having anti-inflammatory, antiseptic, anti-neoplastic, anti-tumor, anti-viral and anti-parasitic properties. Extract of *Q. amara* is used in Aya Champu Espuma, a shampoo available from Nitropharma (Madrid, Spain) used to treat lice.

U.S. Pat. No. 5,676,949 teaches topical application of a *simaba* extract for depigmentation, promoting keratinocyte differentiation, improving cohesion of epidermal cells and more generally preserving or enhancing the protective function of skin and improving the quality of hair. The disclosed *simaba* species are in the same family (Simaroubaceae) as *quassia* species.

*Elaeagnus angustifolia* (also known as the Russian Silverberry, Oleaster, Trebizond Date and Russian olive) is native to western and central Asia and has been introduced to many areas of the US. Its fruit starts out yellow with silver scales and turns red as it ripens. Medicinal food uses of fruits in the genus *Elaeagnus*, including stopping and reversing the growth of cancers is reported in the scientific literature. See, Y S Lee et al. "Antioxidant Activity, Anti-Inflammatory Activity, and Whitening Effects of Extracts of *Elaeagnus multiflora* Thunb." Vol. 10: No. 1, pp. 126-133 (2007). Lee et al. report that *E. multiflora* has anti-inflammatory and whitening (anti-tyrosinase) effects. The use of the fruit of *E. angustifolia* in traditional Iranian medicine as an analgesic and anti-inflammatory agent for joint pain has been reported. H. Hosseinzadeh and R. Rahimi, "Anti-Inflammatory Effects of *Elaeagnus Angustifolia* L. Fruits In Mice And Rats" *Irn. J. Med. Sci*. Vol: 24, No: 3&4, pp. 144-147.

*Portulaca oleracea* is an herbaceous weed with many common names including purslane, pig weed, little hogweed, pusley and vertolaga. Found in many regions of the world, it is rich in omega-3 fatty acids and protein, as well as many biologically active compounds including alkaloids, coumarins, flavonoids, saponin, tryptophan, anthraquinone glycosides, cardiac glycosides and free oxalic acids. In addition to being used as a sedative and analgesic, *P. oleracea* has been reported to be used for treating inflammatory conditions, hyperglycemic and hypertension. Reported dermatological uses include treatment of eczema and warts.

U.S. Pat. No. 7,060,303 (assigned to Avon) teaches a method for decreasing the number and/or depth of facial lines, wrinkles, creases or folds by topically applying to skin a composition comprising an effective amount of a purslane plant, which is taught to include *P. oleracea*. *Portulaca* is one of the ingredients in Avon's Anew Clinical Deep Crease Concentrate with Bo-Hylurox.

US Patent Application Publication No. 2004/0191208 (assigned to Clarins) teaches a cosmetic composition comprising a water-soluble extract of galangal (*Alpinia officinarum*), a water-soluble extract of buffalo grass (*Hierochloe odorata*), and a water-soluble extract of purslane (*P. oleracea*). The water-soluble extract of purslane is further taught to be an extract containing omega-3 fatty acids.

US Patent Application Publication No. 2005/0064049 (assigned to Kao) teaches forty active ingredients as stimulating or facilitating lipolysis of accumulated adipose tissue. Among these is purslane.

*Myrciaria dubia* (also known as the Camu camu and Rumberry) is a shrub found in swampy or flooded areas of the Amazon. Its fruits have a very high vitamin C content—thirty times as much vitamin C as an orange. It is also rich in iron, niacin, thiamin, riboflavin, phosphorus, potassium, beta-carotene, leucine, serine and valine. Nutritional supplements containing Camu camu claim this ingredient as helping to cure viral infections, influenza, the common cold, and autoimmune disorders, as well as aiding in weight loss.

U.S. Pat. No. 7,074,907 teaches a skin care preparation comprising an extract of a purity of at least 90% which is derived from one or more of camu camu fruit juice, camu camu fruit pericarp, camu camu seeds, and mixtures thereof. The disclosed composition is taught to have antioxidant and skin whitening properties.

US Patent Application Publication Nos. 2007/0065396 and 2006/0216251 (both assigned to Tracie Martyn International) teach camu berry as a plant extract rich in Vitamin C that may be incorporated in topical formulations. More particularly, the '396 Publication is directed to topical formulations comprising macqui berry as well as extracts and dermatologically acceptable salts thereof. The '251 Publication is directed to a composition comprising a lipoic acid, a carnitine and a carnosine, or dermatologically acceptable salts of each thereof. The compositions disclosed in both compositions are taught to include exfoliants, including alpha hydroxy acid.

The use of *Platycladus orientalis* (also known as *Biota orientalis*, *Thuja orientalis* and *Oriental arborvitae*) in traditional Chinese medicine was described in the 2700s BCE as calming the five vital yin organs. Prolonged use has been associated with improved complexion, more acute hearing and brightened eyes.

*Amanita muscaria* (also known fly agaric) is a white-spotted red mushroom. Ibotenic acid and muscimol, two constituents of *A. muscaria*, are structurally similar to the neurotransmitters glutamic acid and GABA. *A. muscaria* has also been described in the literature as an herbal muscle relaxant. See, e.g., Manderosian and Liberti eds., *Natural Product Medicine*, pp. 38-42 (Philadelphia, Pa.: G. F. Stickley, 1988). Mushrooms are also rich in glycoalkaloids. See, e.g., Pokorný J., "Natural toxic substances in food" *Cas Lek Cesk.* Vol. 136, No. 9, pp. 267-70 (May 7, 1997).

There remains a need for new and improved methods for reducing the appearance of dynamic facial wrinkles without invasive procedures such as injection or surgery. This need is met by the methods and compositions of the present invention.

SUMMARY OF THE INVENTION

The present invention relates to methods of reducing the appearance of dynamic facial wrinkles by administering oral and/or topical compositions comprising therapeutically-effective amounts of extracts of one or more relaxing herbal agents (RHAs) selected from the group consisting of extracts of *Q. amara*, *E. angustifolia*, *P. oleracea*, *M. dubia*, *P. orientalis* and *A. muscaria*.

The present invention is also directed to methods of reducing the appearance of dynamic facial wrinkles by administering one or more oral and/or topical compositions comprising therapeutically-effective amounts of (i) an RHA selected from the group consisting of extracts of *Q. amara*, *E. angustifolia*, *P. oleracea*, *M. dubia*, *P. orientalis*, *A. muscaria*, and aqueous extracts of plant species from the genus *Valeriana*, *Passiflora*, *Verbascum*, *Scutellaria*, *Cypripedium*, *Magnolia*, *Atriplex* and *Symphytum* and (ii) extracts of an edible solanaceous glycoalkaloid-containing plant or an edible glycoalkaloid-containing fungus ("EGF") selected from plant species in the genus *Solanum* (eggplant, potato, tomato) and mushrooms.

Additionally, the present invention relates to methods of reducing the appearance of dynamic facial wrinkles comprising the steps of (i) exfoliating the skin and (ii) administering oral and/or topical compositions comprising therapeutically-effective amounts of extracts of one or more of the above-listed RHAs alone or in combination with one or more the above-listed ESGPs or EGFs. In this aspect of the invention, the exfoliants may be incorporated into the topical composition or may be incorporated into a separately-applied topical product or process (e.g., microdermabrasion or chemical peel).

The methods of the present invention are particularly directed to the preventing and/or reducing the appearance of "deep" dynamic facial wrinkles. By "deep" is meant wrinkles with a depth of at least 1 mm.

DETAILED DESCRIPTION OF THE INVENTION

A first aspect of the present invention relates to methods of reducing the appearance of dynamic facial wrinkles by administering of oral and/or topical compositions comprising therapeutically-effective amounts of extracts of one or more RHAs selected from the group consisting of *Q. amara*, *E. angustifolia*, *P. oleracea*, *M. dubia*, *P. orientalis* and *A. muscaria*.

In one preferred embodiment of this aspect of the invention, the RHA is an aqueous extract of the bark of *Q. amara* with a quassinoids content of at least about 0.1% by weight. In oral embodiments, the extract of *Q. amara* is administered at a dose of from about 100 mg/day to about 250 mg/day.

In another preferred embodiment of this aspect of the invention, the RHA is an aqueous extract of *E. angustifolia* with a terpene content of at least about 1% by weight of the extract. In oral embodiments, the extract of *E. angustifolia* is administered at a dose of about 25 mg/day.

In a preferred embodiment of this aspect of the invention, the RHA is *P. oleracea* with a content of flavonoids and glycosides of at least about 1% by weight of the extract. In oral embodiments, the extract of *P. oleracea* is administered at a dose of at least about 10 mg/day, preferably at least about 25 mg/day, and more preferably at least about 50 mg/day.

In yet another preferred embodiment of this aspect of the invention, the RHA is an aqueous extract of *M. dubia* with a flavonoid content of at least about 1% by weight of the extract. In oral embodiments, the extract of *M. dubia* is administered at a dose of from about 25 mg/day to about 50 mg/day.

In another preferred embodiment of this aspect of the invention, the RHA is an extract of the seeds of *P. orientalis*. In oral embodiments, the extract of *P. orientalis* is administered at a dose of from about 10 mg/day to about 150 mg/day.

One subset of topical embodiments of this first aspect of the present invention is directed to topical compositions comprising at least one RHA selected from the group consisting of extracts of *Q. amara*, *E. angustifolia*, *M. dubia*, *P. orientalis* and *A. muscaria* which is/are present at a concentration of at least about 0.1% by weight of the composition, preferably at least about 0.5% by weight of the composition.

Another subset of topical embodiments of this first aspect of the present invention is directed to topical compositions comprising an extract of *P. oleracea* at a concentration of at least about 0.1% by weight of the composition, preferably at least about 0.5% by weight of the composition, in combination with at least one an edible solanaceous glycoalkaloid-containing plant selected from plant species in the genus *Solanum* and/or at least one edible glycoalkaloid-containing fungus, preferably a mushroom.

A preferred edible solanaceous glycoalkaloid-containing plant in the genus *Solanum* is selected from the group consisting of *Solanum lycopersicum, Solanum tuberosum* and *Solanum melongena*.

A preferred edible glycoalkaloid-containing fungus is selected from the group consisting of *Rhizomucor miehei, Ganoderma lucidum, Lentinus edodes* and *Grifola frondosa*.

Yet another subset of topical embodiments of this first aspect of the present invention is directed to topical compositions comprising an extract of *P. oleracea* at a concentration of at least about 0.1% by weight of the composition, preferably at least about 0.5% by weight of the composition, in combination with at least one of adenosine and/or L-threonine. Adenosine and/or L-threonine are preferably used at concentrations of less than about 0.5% by weight of the composition, more preferably at concentrations of about 0.2% by weight.

A second aspect of the present invention is directed to methods of reducing the appearance of dynamic facial wrinkles by administering one or more oral and/or topical compositions comprising therapeutically-effective amounts of (i) an RHA selected from the group consisting of extracts of *Q. amara, E. angustifolia, P. oleracea, M. dubia, P. orientalis, A. muscara*, and aqueous extracts of plant species from the genus *Valeriana, Passiflora, Verbascum, Scutellaria, Cypripedium, Magnolia, Atriplex* and *Symphytum* and (ii) an edible solanaceous glycoalkaloid-containing plant selected from plant species in the genus *Solanum* (eggplant, potato, tomato) and/or an edible glycoalkaloid-containing fungus, preferably a mushroom.

In a preferred embodiment of this aspect of the invention, the RHA is administered in an oral dosage form and is an aqueous extract of a plant species in the genus *Valeriana* with a content of valeric acid of at least about 0.8% by weight of the extract. In this embodiment, the *Valeriana* RHA extract is administered at a dose of from about 100 mg/day to about 250 mg/day.

In a particularly preferred embodiment, the *Valeriana* RHA extract is *Valeriana officinalis*.

In another preferred embodiment of this aspect of the invention, the RHA is administered in an oral dosage form and is an aqueous extract of a plant species in the genus *Passiflora* with a content of flavonoids and glycosides of at least about 3% by weight of the extract. In this embodiment, the *Passiflora* RHA extract is administered at a dose of from about 50 mg/day to about 100 mg/day.

In a particularly preferred embodiment, the *Passiflora* RHA extract is *Passiflora incarnate*.

In still another preferred embodiment of this aspect of the invention, the RHA is administered in an oral dosage form and is an aqueous extract of a plant species in the genus *Verbascum* with a glycoside content of at least about 1% by weight of the extract. In this embodiment, the *Verbascum* RHA extract is administered at a dose of from about 50 mg/day to about 100 mg/day.

In a particularly preferred embodiment, the *Verbascum* RHA extract is *Verbascum thapsus*.

In yet another preferred embodiment of this aspect of the invention, the RHA is administered in an oral dosage form and is an aqueous extract of a plant species in the genus *Scutellaria*, with a content of the flavonoid Baicalin at least about 1% by weight of the extract. In this embodiment, the *Scutellaria* RHA extract is administered at a dose of about 25 mg/day to about 50 mg/day.

In a particularly preferred embodiment, the *Scutellaria* RHA extract is *Scutellaria lateriflora*.

In yet another preferred embodiment of this aspect of the invention, the RHA is administered in an oral dosage form and is an aqueous extract of a plant species in the genus *Cypripedium* with a flavonoid content of at least about 1% by weight of the extract. In this embodiment, the *Cypripedium* RHA extract is administered at a dose of about 25 mg/day to about 50 mg/day.

In a particularly preferred embodiment, the *Cypripedium* RHA extract is *Cypripedium pubescens*.

In a further preferred embodiment of this aspect of the invention, the RHA is administered in an oral dosage form and is an aqueous extract of a plant species in the genus *Magnolia* with a honokiol content of at least about 0.5% by weight of the extract. In this embodiment, the *Magnolia* RHA extract is administered at a dose of from about 50 mg/day to about 100 mg/day.

In a particularly preferred embodiment, the *Magnolia* RHA extract is *Magnolia acuminata*

In a still further preferred embodiment of this aspect of the invention, the RHA is administered in an oral dosage form and is an aqueous extract of a plant species in the genus *Atriplex* with an alkaloid content of at least about 0.1% by weight of the extract. In this embodiment, the *Atriplex* RHA extract is administered at a dose of from about 25 mg/day to about 50 mg/day.

In a particularly preferred embodiment, the *Atriplex* RHA extract is *Atriplex hortensis*.

In a still further preferred embodiment of this aspect of the invention, the RHA is administered in an oral dosage form and is an aqueous extract of a plant species in the genus *Symphytum* with an alkaloid content of at least about 2% by weight of the extract. In this embodiment, the *Symphytum* RHA extract is administered at a dose of from about 1 mg/day to about 10 mg/day.

In a particularly preferred embodiment, the *Symphytum* RHA extract is *Symphytum officinale*.

In one preferred embodiment of this aspect of the invention, the RHA is an aqueous extract of *Z. ziziphus* having a tripertene content of at least about 2.5% by weight of the extract. In orally-administered embodiments of the invention, the dose of *Z. ziziphus* is from about 50 mg/day to about 200 mg/day.

In another preferred aspect of this aspect of invention the EGF is a mushroom selected from the group consisting of *Rhizomucor miehei, Ganoderma lucidum* (common name Reishi), *Lentinus edodes* (common name Shiake), *Grifola frondosa* (common name Maitake).

In a particularly preferred embodiment of this aspect of the invention, the EGF is a water-soluble extract of Reishi with a polysaccharide and triterpenoid content of greater than about 1% by weight of the extract. In this embodiment, the EGF is administered at a dose of from about 10 mg/day to about 50 mg/day.

In topical embodiments of this second aspect of the present invention, aqueous extracts of plant species from the genus *Valeriana, Passiflora, Verbascum, Scutellaria, Cypripedium, Magnolia, Atriplex* and *Symphytum* are present at a concentration of at least about 0.1% by weight of the composition, preferably 0.5% by weight of the composition.

Without wishing to be bound by a theory, applicant believes that ESGPs and/or EGFs potentiate the action of the claimed RHAs by inhibiting metabolism of ACh and thereby increasing the extent of reduction of the appearance of dynamic wrinkles (i.e., in terms of number, length and/or depth of wrinkles). ESGPs and EGFs may also potentiate the action of the claimed RHAs by increasing the duration of the treatment in a manner such that treatments can be more temporally spaced (e.g., once every second or third day versus once per day).

Preferred embodiments of this aspect of the present invention are directed to methods for reducing the appearance of dynamic facial wrinkles comprising administering an oral or topical composition comprising a therapeutically-effective amount of (i) at least two RHAs selected from the group consisting of an extract of *Z. ziziphus, V. officinalis, Q. amara*, and *P. oleracea* and (ii) at least one ESGP selected from an extract of a species in the genus *Solanum* or a water-soluble extract of *Ganoderma lucidum*.

Other preferred embodiments of this aspect of the present invention are directed to methods for reducing the appearance of dynamic facial wrinkles comprising the steps of administering two or more oral or topical compositions which in combination comprise therapeutically-effective amounts of (i) at least two RHAs selected from the group consisting of an extract of *Z. ziziphus, V. officinalis, Q. amara*, and *P. oleracea* and (ii) at least one ESGP or EGF selected from an extract of a species in the genus *Solanum* or a water-soluble extract of *Ganoderma lucidum*.

The methods described in the first and second aspects of the invention may comprise as part of the topical composition one or more topical exfoliating agents as described in the third aspect of the invention.

A third aspect of the present invention is directed to methods of reducing the appearance of dynamic facial wrinkles comprising the steps of (i) exfoliating the skin and (ii) administering oral and/or topical compositions according to the first and second aspects of the invention—namely, administration of therapeutically-effective amounts of extracts of one or more of the above-listed RHAs alone or in combination with one or more the above-listed ESGPs and/or EGFs. In this aspect of the invention, the method of exfoliating is such that one to two hours after the exfoliation, there is an increase in transepidermal water loss (TEWL) of at least about 50%, preferably at least about 100%.

One preferred embodiment of the first aspect of the invention (reducing the appearance of dynamic facial wrinkles by oral and/or topical administration of a composition comprising a therapeutically-effective amount of at least one RHA selected from the group consisting of extracts of *Q. amara, E. angustifolia, P. oleracea, M. dubia, P. orientalis* and *A. muscaria*) is directed to exfoliating the skin by application of one or more topical exfoliating agents well known to those of skill in the art non-limiting examples of which include alpha-, beta- and poly-hydroxy acids (including the patents to Van Scott and Yu discussed in the Background section) as well as abrasive beads (e.g., polyethylene).

In a particularly preferred embodiment of this first aspect of the invention, the topical exfoliating agent comprises one or more acid protease enzymes in combination with an acidic buffering system as described in U.S. Pat. Nos. 5,976,556; 6,569,437; and 6,656,701.

Another preferred embodiment of this first aspect of the invention is directed to exfoliating the skin by a chemical peel administered by a physician, aesthetician or other licensed skin care professional. Non-limiting examples of such peels include tricholoracetic acid (at a concentration of up to about 35%) and Jessner's solution.

Another preferred embodiment of this first aspect of the invention is directed to exfoliating the skin by microdermabrasion, a procedure skin where jets of aluminum oxide or corundum crystals are sprayed on to the face and then suctioned together with sloughed-off skin.

With respect to the second aspect of the invention (reducing the appearance of dynamic facial wrinkles by oral and/or topical administration of a composition comprising a therapeutically-effective amount of at least one RHA selected from the group consisting of extracts of *Valeriana, Passiflora, Verbascum, Scutellaria, Cypripedium, Magnolia, Atriplex* and *Symphytum*), a preferred embodiment is directed to the administration of a topical composition comprising as an exfoliating agent one or more acid protease enzymes in combination with an acidic buffering system as described in U.S. Pat. Nos. 5,976,556; 6,569,437; and 6,656,701.

A particularly preferred embodiment of the second aspect of the present invention is directed to a method of reducing the appearance of dynamic facial wrinkles comprising administering (i) a therapeutically-effective amount of at least one RHA selected from the group consisting of extracts of *Valeriana, Passiflora, Verbascum, Scutellaria, Cypripedium, Magnolia, Atriplex* and *Symphytum* (ii) an ESGPs and/or EGFs and (iii) a topical composition comprising as an exfoliating agent one or more acid protease enzymes in combination with an acidic buffering system as described in U.S. Pat. Nos. 5,976,556; 6,569,437; and 6,656,701.

A fourth aspect of the present invention is directed to the treatment of dynamic facial wrinkles that have stress as a contributing causal factor. As used in the present invention, stress is considered to be a contributing causal factor if the consumer or patient scores a certain minimal level on a self-administered questionnaire as described in Example 1 below.

A fifth aspect of the present invention is directed to the use of adenosine or L-threonine in combination with the topical and oral compositions of the first four aspects of the invention. Without wishing to be bound by a theory, applicant believes that adenosine and L-threonine potentiate the action of the RHA(s), alone or in combination with one or more ESGP(s) and/or EGF(s), by inhibiting the action of acetyl cholinesterase and thereby inhibiting muscle contraction.

In topical formulations, adenosine and/or L-threonine are preferably used at concentrations of less than about 0.5% by weight of the composition, more preferably at concentrations of about 0.2% by weight. In oral compositions, adenosine and/or L-threonine are preferably used at concentrations of about 2% by weight.

Dosing and Dosage Forms

As will be appreciated by those of skill in the art, the amount(s) of active ingredients (RHAs, ESGPs, EGFs) which constitute a therapeutically-effective dose will vary based on the depth, length and number of dynamic facial wrinkles, other skin and health conditions (past and present), and route(s) of administration. Dose frequency of RHAs, ESGPs and EGFs will also vary based on the type of exfoliating treatment. Suitable dosing regimens can be readily selected by those skilled in the art, taking into consideration these factors.

By way of non-limiting example, a topical product comprising 1% RHAs, ESGPs and/or EGFs may be administered daily, whereas a product comprising 30% of the same active ingredients (RHAs, ESGPs, EGFs) may be administered 2-3 times per week, while a product comprising 60% actives may be administered once per week.

Preferred oral unit daily doses vary among the RHAs, ESGPs and EGFs, and range from about 1 mg/day to 500 mg/day.

Preferably, the methods of treatment of the first, second, third and fourth aspects of the invention as described above are administered on a daily basis for a period of at least two weeks.

Oral dosage forms may be in the form of tablets, troches, cachet, teas, dispersions, suspensions, solutions, capsules, gel caps, caplets, compressed tablets, etc. according to methods known to those of skill in the art and described in *Remington's Science and Practice of Pharmacy* 20$^{th}$ ed. (Baltimore, Md.: Lippincott (2000). Because of their ease of administration, tablets and capsules are a preferred solid oral dosage form. If desired, tablets may be coated using standard aqueous or nonaqueous techniques.

Topical dosage forms may be creams, lotions, gels, serums in solution or suspension in an aqueous liquid or anhydrous liquid, or in a two or three phase emulsion (oil-in-water, water-in-oil, water-in-silicone, silicone-in-water, oil-in-water-in-oil or water-in-oil-in-water).

A preferred topically-applied dosage of compositions comprising RHAs and/or ESGP and EGF is about 2 mg/cm$^2$.

Additionally, the RHA, ESGP and EGF active ingredients may be formulated in a cosmetically-acceptable hydroalcoholic vehicle having from about 40% to about 75%, preferably from 55% to 65%, by weight of water and from about 60% to about 25%, preferably from 45% to about 35% by weight of an aliphatic alcohol. While various lower aliphatic alcohols, both monohydric and polyhydric, may be used, ethanol and propanol are more preferred.

RHAs, ESGPs and/or EGFs may be administered through transdermal patches according to methods known to those of skill in the art and described in *Remington's Science and Practice of Pharmacy*.

Extraction Methods

The plant or fungus body or if desired specific plant or fungus parts (collectively referred to below as the "plant body") are cut into small pieces or ground into a powder. During a typical extraction process, the plant body is placed in a Soxhlet extractor and extracted with any suitable solvent. Typical solvents include, but are not limited to, water, lower alcohols and mixtures thereof. The solvent is maintained at reflux and the plant body is extracted, typically for a period of from about 6 hours to about 48 hours. The solvent is then separated from the extract either under low pressure or by evaporation, leaving a residue containing the desired plant extract. The residue may be diluted and purified using techniques known to those of skill in the art including by gravity chromatography.

An alternative extraction process likewise involves immersing ground, finely cut or macerated plant body in a solvent bath comprising water and/or lower alcohol(s). The mixture of plant body and solvent is allowed to sit for a period of from about 6 hours to about 48 hours. The mixture is then filtered, separating the solids from the filtrate. The collected solids are then immersed in a solvent bath as described above. That mixture is separated by filtration. The filtrates from both extractions are combined, and concentrated under reduced pressure to obtain a residue. The residue is vacuum dried for about 1 to about 10 hours, preferably for about 1 to about 2 hours at room temperature. The above procedure can be modified by placing the plant body (after grinding/maceration) into a sachet, tea bag or similar enclosure known to those of skill in the art.

A still further extraction process involves adding the ground/macerated plant body to a solvent system (preferably, water and/or lower alcohol(s)), in a ratio of from about 4:1 to about 7:1 by volume to form a mixture. That mixture is then heated to a temperature of about one degree Celsius below the boiling point of the solvent system and stirred for about an hour. The mixture is filtered and the filtrate is washed with fresh solvent in a volume ratio of about 1:1. The filtrate is then concentrated by forced drying, pressure, heat or other techniques known to those of sill in the art. Preferred solvents include ethanol, methanol, propanol, 2-propanol, water and mixtures thereof.

Supplemental Ingredients

The International Cosmetic Ingredient Dictionary and Handbook, (11th Edition), published by the Cosmetics Fragrance and Toiletries Association, describes a wide variety of non-limiting ingredients used in topically-applied personal care and dermatologic products, which may be formulated in compositions of the present invention. These include skin care actives by which is meant ingredients that help to reduce the appearance of and/or prevent the formation of fine lines, wrinkles, age spots, sallowness, blotchiness, redness, dark circles (i.e., under the eyes) as well as ingredients that help to reduce skin oiliness, reduce transepidermal water loss, improve skin retention of moisture and/or improve skin elasticity. Non-limiting examples of skin care actives include: anti-inflammatory agents; humectants; skin bleaching/lightening agents; skin soothing agents; antioxidants; vitamins and derivatives thereof; short-chain peptides (i.e., having less than about 12 amino acids); and self-tanning agents.

The topical compositions of the present invention may also contain plasticizers, structuring agents, viscosity modifiers, thickener and gallants, as further described in U.S. Pat. Nos. 6,492,326 and 6,277,892 and U.S. Patent Application Publication Nos. 2004/0180020 and 2005/0142095.

EXAMPLES

The following examples are further illustrative of the present invention. The components and specific ingredients are presented as being typical, and various modifications can be derived in view of the foregoing disclosure within the scope of the invention.

Example 1

Stress Questionnaire

One aspect of the present invention is directed to reducing the dynamic facial wrinkles caused at least in part by stress. Stress is considered to be a contributing causal factor to dynamic facial wrinkles for individuals with a score of at least 105 on the following self-administered questionnaire. Study participants are asked to indicate on a scale of 1-5 the frequency of occurrence of the following thirty six conditions (physical and psychological) and behaviors: (1)—never; (2) rarely; (3) sometimes; (4) frequently; (5) almost daily.

Physical conditions: (a) headache; (b) increase in heart beat; (c) allergy; (d) indigestion; (e) grinding teeth; (f) neckache; (g) backache; (h) fatigue/exhaustion; (i) sweaty hands & feet; (j) stomach-ache; (k) trembling; (l) tightness in chest.

Psychological conditions: (a) difficulty in relaxing; (b) easily angered; (c) dejected; (d) difficulty in concentration; (e) indecisiveness; (f) anxiety; (g) frustration; (h) hostility; (i) impatience; (j) racing thoughts; (k) insomnia; (l) emotional imbalance.

Behaviors: (a) strained relationships; (b) difficulty in laughing; (c) eat more or less than usual; (d) go quiet; (e) sexual difficulties; (f) smoke or drink more than usual; (g)

drive recklessly; (h) want change; (i) work becoming a load; (j) escape responsibilities; (k) use medications too often; (l) try to avoid situations.

Example 2

RHA+ESGP Oral Supplement Capsule

|  |  |
|---|---|
| *Valeriana officinalis* | 150 mg |
| *Ziziphus ziziphus* | 150 mg |
| *Passiflora incarnate* | 50 mg |
| *Portulaca oleracea* | 50 mg |
| *Ganoderma lucidum* | 50 mg |
| *Solanum melongena* | 50 mg |
| *Solanum lycopersicum* | 50 mg |
| *Myrciaria dubia* | 50 mg |
| L-Threonine | 2 mg |
| Adenosine | 2 mg |

The above-listed ingredients are filled into a two-piece hard capsule, in which case the separate ends of the capsule are filled with dried herb and the capsule assembled by techniques well-known to those of skill in the art. Other encapsulation techniques known in the art and described in the patents incorporated herein by reference may also be used.

Example 3

RHA Eye Cream

| Part A |  |
|---|---|
| Deionized Water | 47.650% |
| Acrylates/C10-30 Alkyl Acrylate Crosspolymer | 0.300% |
| Panthenol | 0.100% |
| Potassium Sorbate | 0.100% |
| Disodium EDTA | 0.100% |
| Allantoin | 0.100% |
| *Aloe Barbadensis* Leaf Juice (Activera 10X, Active Organics) | 5.000% |
| Part B |  |
| Caprylic/Capric Triglyceride | 2.000% |
| Dimethicone | 3.000% |
| *Butyrospermum Parkii* (Shea Butter) | 2.000% |
| *Carthamus Tinctorius* (Safflower) Seed Oil | 2.000% |
| Cetearyl Alcohol | 1.500% |
| Dimethiconol | 1.300% |
| Steareth-2 | 1.000% |
| Steareth-21 | 0.500% |
| Tocopheryl Acetate | 0.100% |
| Cyclomethicone | 5.000% |
| Part C |  |
| Triethanolamine | 0.250% |
| Part D |  |
| Carbomer 940 2% Solution | 10.000% |
| Part E |  |
| Actizyme MCS (Active Organics) | 5.000% |
| Part F |  |
| Sodium Hyaluronate (Actimoist Bio 2, Active Organics) | 2.000% |
| Phenonip | 1.000% |
| Part G |  |
| RHA/ESGP/EGF Complex | 10.000% |
| *Valeriana officinalis* | 1.0 |
| *Ziziphus ziziphus* | 3.0 |
| *Quassia amara* | 1.0 |
| *Portulaca oleracea* | 1.0 |
| *Ganoderma lucidum* | 1.8 |
| *Solanum melongena* | 2.0 |
| L-Threonine | 0.1 |
| Adenosine | 0.1 |

Add ingredients in Parts A and B at 80° C. in separate vessels with mixing. Combine and mix Parts A and B until smooth. Decrease temperature to 60° C. Add Parts C and D to Parts A/B with mixing until smooth. Decrease temperature to temperature to 40° C. Add Parts E, F and G sequentially to Parts A/B/C/D with mixing.

Example 4

RHA Serum

| Part A |  |
|---|---|
| Deionized Water | 70.850% |
| Keltrol RD | 0.250% |
| Butylene Glycol | 0.400% |
| Part B |  |
| Water | 0.600% |
| Potassium Sorbate | 0.100% |
| Part C |  |
| Water, Algae Extract, and *Aloe Barbadensis* Leaf Juice (Actisea 100, Active Organics) | 5.0% |
| Part D |  |
| *Aloe Barbadensis* Leaf Juice (Activera 10x, Active Organics) | 5.000% |
| Phenoxyethanol | 0.600% |
| Neolone 950 | 0.050% |
| Actizyme MCS | 5.000% |
| Part E |  |
| Water | 2.000% |
| Allantoin | 0.1% |
| Disodium EDTA | 0.05% |
| Part F |  |
| RHA/ESGP/EGF Complex (Example 3, Part G) | 10.000% |

Combine ingredients in Part A with agitation and heating to 60° C. and mix until smooth. Add Part B ingredients to Part A with continual agitation until smooth. Add Part C ingredients to Parts A/B. Decrease temperature to 40° C. and add Part D ingredients to Parts A/B/C with agitation until smooth. Remove all heat and add Parts E and F ingredients sequentially to Parts A/B/C/D with agitation until smooth. Continue mixing until room temperature.

Example 5

RHA Exfoliating Facial Cream

| Part A |  |
|---|---|
| Deionized Water | 52.600% |
| Magnesium Aluminum Silicate | 0.400% |
| Xanthan Gum | 0.150% |
| Acrylates/C10-30 Alkyl Acrylate Crosspolymer | 0.750% |

-continued

Part B

| | |
|---|---|
| Butylene Glycol | 4.000% |
| Disodium EDTA | 0.050% |

Part C

| | |
|---|---|
| Hydrogenated Lecithin | 0.500% |
| Caprylic/Capric Triglyceride | 8.000% |
| *Simmondsia Chinensis* (Jojoba) Seed Oil | 5.000% |
| Octyl Palmitate | 4.000% |
| Cetearyl Alcohol | 2.000% |
| PEG-8 Stearate | 1.000% |
| PEG-100 Stearate | 0.800% |

Part D

| | |
|---|---|
| Triethanolamine 99% | 0.100% |

Part E

| | |
|---|---|
| *Aloe Barbadensis* Leaf Juice (Activera 10x, Active Organics) | 5.000% |
| Phenoxyethanol | 0.500% |
| Potassium Sorbate | 0.100% |
| Methylisothiazolinone | 0.050% |
| *Mucor Miehei* Extract, Butylene Glycol, and N-Acetylglucosamine (Actizyme MCS, Active Organics) | 5.000% |

Part F

| | |
|---|---|
| RHA/ESGP/EGF Complex (Example 3, Part G) | 10.000% |

Mix ingredients in Parts A, B and C at 80° C. in separate vessels. Mix Parts A and B until smooth, then add Part C. Decrease temperature to 60° C. and then add Part D with mixing until smooth. Decrease temperature to 40° C. and adding Parts E and F sequentially with mixing.

Example 6

RHA Exfoliating Toner

| | |
|---|---|
| Deionized Water | 83.190% |
| Methyl Gluceth-20 | 1.000% |
| Potassium Sorbate | 0.100% |
| Sodium Benzoate | 0.100% |
| Phenoxyethanol | 0.600% |
| Citric acid | 0.010% |
| Glycolic Acid | 5.000% |
| RHA/ESGP/EGF Complex (Example 3, Part G) | 10.000% |

Mix all ingredients in the sequence listed above with agitation at 40° C. When formula is smooth and homogenous, begin cooling to room temperature with agitation.

Example 7

RHA Mask

Part A

| | |
|---|---|
| Deionized Water | 49.960% |
| *Aloe Barbadensis* Leaf Juice (Activera 10X, Active Organics) | 5.000% |
| Glycerin | 4.000% |
| Caffeine | 0.100% |
| *Acacia* Gum | 0.300% |
| Chromium Oxide Green | 0.500% |
| Titanium Dioxide | 3.000% |
| Methylparaben | 0.200% |

-continued

Part B

| | |
|---|---|
| Glyceryl Stearate | 6.000% |
| *Simmondsia Chinensis* (Jojoba) Seed Oil | 1.500% |
| Tocopheryl Acetate | 0.100% |
| Propylparaben | 0.100% |

Part C

| | |
|---|---|
| Bentonite | 11.00% |

Part D

| | |
|---|---|
| Phenoxyethanol | 0.500% |
| Citric Acid | 2.100% |
| Actizyme MCS (Active Organics) | 5.000% |

Part E

| | |
|---|---|
| EO Spearmint | 0.070% |
| EO Peppermint | 0.070% |

Part F

| | |
|---|---|
| RHA/ESGP/EGF Complex (Example 3, Part G) | 10.000% |

Mix ingredients in Parts A and B at 80° C. in separate vessels. Mix Parts A and B until smooth. Decrease temperature to 60° C., then add Part C with mixing until smooth. Decrease temperature to 40° C. and adding Parts D, E and F sequentially with mixing.

Example 7

Clinical Assessment of Reduced Dynamic Wrinkles

Seventy five female subjects (average age 55) identified via questionnaire (Example 1) as being under stress are enrolled to complete a three-month double blind trial to evaluate the effectiveness of a topical and oral products comprising RHAs and/or ESGPs on skin properties. Prior to enrollment, all panelists sign informed consent forms.

Twenty-five subjects (Panel A) are administered once daily an oral composition (Example 2), and apply twice daily a topical exfoliating cream (Example 5). Two additional panels, each comprising twenty-five subjects and matched to Panel A based on age and skin type, follow a similar regimen except in one group (Panel B) a placebo oral composition is administered, while in the other (Panel C) a placebo cream is applied.

Subjects are evaluated throughout the study for changes in moisturization (impedance), superficial lines and wrinkles (SFL using the Packman method), global age assessment, skin firmness (Ballistometry), skin replica analysis of deeper lines and wrinkles, skin oiliness and clarity. In addition panelists are asked to complete a self-assessment questionnaire at the conclusion of the study.

After three months, each group shows some reduction in lines and wrinkles assessed either via the SFL scoring method, skin replica analysis or self-assessment questionnaires. Reduction in SFLs is greater in Panel A (37%), than Panels B and C (15% and 22% respectively). Skin replica analysis of deeper lines and wrinkles, demonstrates a 27% reduction for Panel A, and 11% and 22% reductions for Panels B and C respectively. Analysis of self-assessment surveys yield similar results with Panel A responding more favorably than Panels B or C. No significant changes in sebum levels or skin clarity are observed. Each panel shows modest and equivalent improvements in skin moisture levels, attributable to the moisturizing action of topical treatment. No significant changes in skin firmness are observed. Each panel also shows decrease in stress levels based upon survey, with Panels A and C showing a greater improvement than Panel B.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A method for reducing the appearance of dynamic facial wrinkles in a human comprising orally administering to a human in need thereof an oral composition comprising a therapeutically-effective amount of an extract of *Quassia amara* and a therapeutically-effective amount of an extract of *Elaeagnus angustifolia*.

2. The method of claim 1 wherein the oral composition is administered at least once daily.

3. The method of claim 2 wherein the oral composition is administered at least once daily for at least two weeks.

4. The method of claim 2 wherein the oral composition is administered at a dose of at least about 25 mg/day.

5. The method of claim 1 wherein the oral composition further comprises an extract of at least one edible solanaceous glycoalkaloid-containing plant in the genus *Solanum* selected from the group consisting of *Solanum lycopersicum*, *Solanum tuberosum* and *Solanum melongena* or an edible glycoalkaloid-containing fungus selected from the group consisting of *Rhizomucor miehei*, *Ganoderma lucidum*, *Lentinus edodes* and *Grifola frondosa*.

6. The method of claim 1 further comprising an exfoliating step selected from the group consisting of
   i. topical application to the area of the skin having dynamic facial wrinkles a topical composition comprising a topical exfoliating agent selected from the group consisting of alpha hydroxy acids, beta hydroxy acids, polyhydroxy acids and acid protease enzymes;
   ii. microdermabrasion of the area of the skin having dynamic facial wrinkles; and
   iii. topical application to the area of the skin having dynamic facial wrinkles a chemical peel.

7. The method of claim 1 wherein the oral composition further comprises a therapeutically-effective amount of at least one of adenosine or L-threonine.

8. The method of claim 1 wherein the oral composition further comprises a therapeutically-effective amount of an extract of *Amanita muscaria*.

9. The method of claim 5 wherein the oral composition comprises an extract of *Solanum lycopersicum*.

10. The method of claim 5 wherein the oral composition comprises an extract of Lentinus edodes.

* * * * *